United States Patent [19]

Loutfy et al.

[11] Patent Number: 4,808,506

[45] Date of Patent: Feb. 28, 1989

[54] PHOTOCONDUCTIVE IMAGING MEMBERS WITH IMIDAZOLE PERINONES

[75] Inventors: Rafik O. Loutfy, Willowdale; Peter M. Kazmaier, Mississauga; Ah-Mee Hor, Mississauga; Richard A. Burt, Mississauga, all of Canada

[73] Assignee: Xerox Corporation, Stamford, Conn.

[21] Appl. No.: 86,333

[22] Filed: Aug. 17, 1987

[51] Int. Cl.[4] .............................................. G03G 5/06
[52] U.S. Cl. .......................................... 430/59; 430/73
[58] Field of Search ................................ 430/59, 78, 73

[56] References Cited

U.S. PATENT DOCUMENTS

| | | | |
|---|---|---|---|
| 3,871,882 | 3/1975 | Weidemann | 430/59 |
| 3,879,200 | 4/1975 | Regensburger et al. | 96/1.5 |
| 4,517,270 | 5/1985 | Graser et al. | 430/58 |

FOREIGN PATENT DOCUMENTS

| | | | |
|---|---|---|---|
| 5959692 | 2/1976 | Japan | . |
| 5958433 | 4/1984 | Japan | . |

*Primary Examiner*—John L. Goodrow
*Attorney, Agent, or Firm*—E. O. Palazzo

[57] ABSTRACT

Disclosed is an improved layered photoresponsive imaging member comprised of a supporting substrate; an imidazole perinone comprised of components with a mixture of cis and trans isomers of Formulas III, IV, and V, including trans indanthrene Brilliant Orange, cis indanthrene Bordeaux Red; bis(4,5-dimethyl)benzimidazole perinone and bis 2,3 naphthimidazole perinone, and an aryl amine hole transport layer comprised of molecules of the following formula:

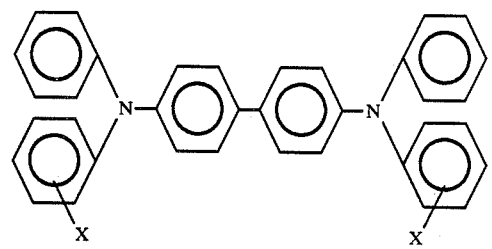

dispersed in a resinous binder and wherein X is selected from the group consisting of halogen and alkyl.

30 Claims, 2 Drawing Sheets

PHOTOCONDUCTIVE IMAGING MEMBERS WITH IMIDAZOLE PERINONES

BACKGROUND OF THE INVENTION

This invention is generally directed to photoresponsive imaging members, and more specifically the present invention is directed to layered photoresponsive members having incorporated therein certain imidazole perinone pigment compositions. Thus, in one embodiment the present invention envisions the selection of specific imidazole perinone pigment compositions as organic photogenerator materials in photoresponsive imaging members containing therein arylamine hole transport molecules. The aforementioned photoresponsive imaging members can be negatively charged when the perinone photogenerating layer is situated between the hole transport layer and the substrate; or positively charged when the hole transport layer is situated between the photogenerating layer and the supporting substrate. Additionally, the photoresponsive imaging members with the perinone pigment compositions as photogenerator substances, and wherein the member further includes therein an aryl amine hole transport layer are useful in electrophotographic imaging processes, especially xerographic processes wherein negatively charged or positively charged images are rendered visible with developer compositions of the appropriate charge.

Layered photoresponsive imaging members are generally known, reference for example U.S. Pat. No. 4,265,900, the disclosure of which is totally incorporated herein by reference, wherein there is described an imaging member comprised of a photogenerating layer, and an aryl amine hole transport layer. Examples of substances useful in the photogenerating layer of this patent include trigonal selenium, metal phthalocyanines, and metal free phthalocyanines. Additionally, there is described in U.S. Pat. No. 3,121,006 a composite xerographic photoconductive member comprised of finely divided particles of a photoconductive inorganic compound dispersed in an electrically insulating organic resin binder. The binder components disclosed in the '006 patent comprise a material which is incapable of transporting for any significant distance injected charge carriers generated by the photoconductive particles. Illustrative examples of specific binder materials disclosed in the '006 patent include polycarbonate resins, polyester resins, polyamide resins, and the like.

Many other patents are in existence describing photoresponsive devices including layered devices containing generating substances, such as U.S. Pat. No. 3,041,167, which discloses an overcoated imaging member with a conductive substrate, a photoconductive layer, and an overcoating layer of an electrically insulating polymeric material. This member is utilized in an electrophotographic copying method by, for example, initially charging the member with an electrostatic charge of a first polarity, and imagewise exposing to form an electrostatic latent image which can be subsequently developed to form a visible image. Prior to each succeeding imaging cycle, the imaging member can be charged with an electrostatic charge of a second polarity, which is opposite in polarity to the first polarity. Sufficient additional charges of the second polarity are applied to create across the member a net electrical field of the second polarity. Simultaneously, mobile charges of the first polarity are created in the photoconductive layer such as by applying an electrical potential to the conductive substrate. The imaging potential, which is developed to form the visible image, is present across the photoconductive layer and the overcoating layer.

Photoresponsive imaging members with squaraine photogenerating pigments are also known, reference U.S. Pat. No. 4,415,639, the disclosure of which is totally incorporated herein by reference. In this patent there is illustrated an improved photoresponsive imaging member with a substrate, a hole blocking layer, an optional adhesive interface layer, an organic photogenerating layer, a photoconductive composition capable of enhancing or reducing the intrinsic properties of the photogenerating layer, and a hole transport layer. As photoconductive compositions for the aforementioned member, there can be selected various squaraine pigments, including hydroxy squaraine compositions. Moreover, there are disclosed in U.S. Pat. No. 3,824,099 certain photosensitive hydroxy squaraine compositions. According to the disclosure of this patent, the squaraine compositions are photosensitive in normal electrostatographic imaging processes.

The use of selected perylene pigments as photoconductive substances is also known. There is thus described in Hoechst European Patent Publication No. 0040402, DE3019326, filed May 21, 1980, the use of N,N'-disubstituted perylene-3,4,9,10,-tetracarboxyldiimide pigments as photoconductive substances. Specifically, there is disclosed in this publication evaporated N,N'-bis(3-methoxypropyl)perylene-3,4,9,10-tetracarboxyldiimide dual layered negatively charged photoreceptors with improved spectral response in the wavelength region of 400 to 700 nanometers. A similar disclosure is revealed in Ernst Gunther Schlosser, Journal of Applied Photographic Engineering, Vol. 4, No. 3, page 118 (1978). There are also disclosed in U.S. Pat. No. 3,871,881 photoconductive substances comprised of specific perlyene-3,4,9,10-tetracarboxylic acid derivative dyestuffs. In accordance with the teachings of this patent, the photoconductive layer is preferably formed by vapor depositing the dyestuff in a vacuum. Also, there is specifically disclosed in this patent dual layer photoreceptors with perylene-3,4,9,10-tetracarboxylic acid diimide derivatives, which have spectral response in the wavelength region of from 400 to 600 nanometers.

In U.S. Pat. No. 3,879,200 there are illustrated imaging members with perinones similar to some of the perinones of the present invention; however, this patent is silent with respect to layered imaging members with aryl amine hole transport layers. The aforementioned members of the present invention have advantages not possessed or disclosed in the '200 patent including, for example, improved electrical performance, and in some situations photosensitivity enhanced spectral response. Furthermore, layered imaging members with imidazole thiazinoperinone photogenerators and related components are illustrated in U.S. Pat. No. 4,517,270, and in Japanese Laid Open Publication Nos. 59-58433/84, and 59-59692/84. The aforementioned members of the present invention have advantages not possessed or disclosed in the Japanese publications, including improved electrical performance and increased spectral response as illustrated herein. The aforementioned advantages and other improvements achievable with the layered photoresponsive imaging member of the present invention reside primarily in the selection of the specific photogenerating pigments, particularly in a purified form, and the incorporation thereof into the imaging members with certain aryl amine compounds as charge transport layers, which aryl amines are more fully illustrated hereinafter.

While the above-described photoresponsive imaging members are suitable for their intended purposes, there continues to be a need for improved members, particularly layered members, having incorporated therein specific perinone pigment compositions and aryl amine hole transport compounds. Additionally, there continues to be a need for layered imaging members with acceptable visible sensitivity, low dark decay characteristics, high charge acceptance values comprised of specific aryl amine charge transport compositions; and as photogenerating materials perinone pigments; and wherein these members can be used for a number of imaging cycles in a xerographic imaging or printing apparatus. Furthermore, there continues to be a need for photoresponsive imaging members which can be positively or negatively charged thus permitting the development of images, including color images, with positively or negatively charged toner compositions. Moreover, there continues to be an important need for disposable imaging members with nontoxic organic pigments. Also, there is a need for disposable imaging members useful in xerographic imaging processes, and xerographic printing systems wherein, for example, light emitting diodes (LED), helium cadmium, or helium neon lasers are selected; and wherein these members are particularly sensitive to the visible region of the spectrum, that is, from about 400 to about 700 nanometers. Also, there is a need for low cost, high quality imaging members wherein reduced amounts of photosensitive materials can be selected.

SUMMARY OF THE INVENTION

It is an object of the present invention to provide improved photoresponsive imaging members which are substantially inert to the users thereof.

It is yet another object of the present invention to provide disposable layered photoresponsive imaging members.

A further specific object of the present invention resides in the provision of an improved photoresponsive imaging member with an aryl amine hole transport layer, and a photogenerator layer comprised of specific perinone pigment compositions.

In yet another specific object of the present invention there are provided negatively charged layered photoresponsive imaging members comprised of vacuum evaporated perinone pigment compositions optionally dispersed in a resinous binder, and thereon a hole transport layer comprised of aryl amine molecules.

There are provided in another object of the present invention positively charged layered photoresponsive imaging members with a top vacuum evaporated perinone pigment composition optionally dispersed in a resinous binder, and thereunder a hole transport layer comprised of aryl amine molecules.

It is still another object of the present invention to provide improved imaging members sensitive to light in the visible region of the spectrum, that is, from about 400 to about 700 nanometers.

It is yet another object of the present invention to provide imaging and printing methods with the improved photoresponsive imaging members illustrated herein.

Another object of the present invention resides in providing imaging members for high speed printing and imaging processes, which members can be utilized for extended time periods.

These and other objects of the present invention are accomplished by the provision of photoresponsive imaging members having incorporated therein photogenerating layers comprised of perinone pigment compositions selected from the group consisting of I. cis and/or trans isomers of the formulas Formula I II. cis and trans isomers of the formulas Formula II wherein R is a hydrogen substituent, alkyl, aryl, substituted alkyl, and substituted aryl, and the like; and x is a halogen, nitro or cyano substituent.

III.

Formula III

(Trans)Indanthrene Brilliant orange (Vat Red 7)

(Cis)Indanthrene Bordeaux (Vat Red 15)

Illustrative examples of specific photogenerating imidazole perinone pigments in addition, for example, to those represented by Formula III useful for incorporation into the imaging members of the present invention include those of the following formulas:

IV.

2,3,11,12-tetramethyl bis benzimidazo[2,1-b:2',1'-2']benzo[lmn][3,8]phenanthroline-8,17 dione, and 2,3,12,13-tetramethyl bis benzimidazo[2,1-b:1',2'-j]benzo[lmn][3,8]phenanthroline-6,9-dione(bis(4,5-dimethyl)benzimidazole perinones)

Formula IV

V.

Formula V bis naphthimidazole perinone

The known benzimidazole perinone compositions of Formula III illustrated herein can generally be prepared by the condensation reaction of 1,4,5,8-naphthalene-tetracarboxylic dianhydride with an o-phenylene diamine, followed by the isolation of the cis from the trans isomer thereof by the preferential crystallization of their salts with alcoholic potassium hydroxide. More specifically, the trans and cis benzimidazole perinones of Formula III are commercially available from Hoechst Chemical Corporation as Indanthrene Brilliant Orange GR (Vat Orange 7) and Indanthrene Bordeaux RR (Vat Red 15), respectively.

Other perinone pigments of the present invention can be prepared by the condensation reaction of 1,4,5,8-naphthalene-tetracarboxylic acid or its corresponding anhydrides with an amine in a molar ratio of from about 1:2 to about 1:10, and preferably in a ratio of from about 1:2 to about 1:3. This reaction is generally accomplished at a temperature of from about 130° C. to about 270° C., and preferably at a temperature of about 210° C. with stirring and in 1-chloronaphthalene or acetic acid in the presence of a catalyst. Subsequently, the desired product is isolated from the reaction mixture by known techniques such as filtration. The resultant perinone pigments are further purified by fractional sublimation which involves subjecting the pigment to a temperature of from about 300° to 550° C., whereby impurities and decomposition products more volatile than the desired components are separated at a temperature zone of below 300° C., and there are obtained the purified perinone components at a purity of at least 95 percent at a temperature zone of from about 350° to 500° C. separated from the nonvolatile impurities which remain at the high temperature (550° C.) zone. Additionally, the other perinones illustrated herein can be purified by the aforementioned process. Examples of reactants include 1,4,5,8-naphthalene-tetracarboxylic acid, and 1,4,5,8-naphthalene-tetracarboxylic acid dianhydride. Illustrative amine reactants include o-phenylene diamine; 2,3-diamino naphthalene; 2,3-diamino pyridine; 3,4-diamino pyridine; 5,6-diamino pyrimidine; 9,10-diamino phenanthrene; 1,8-diamino naphthalene; aniline; substituted anilines; and 4,5-dimethyl ortho phenylene diamine. Catalysts that can be selected, present in an amount of from about 1 to about 5 percent by weight, include known effective materials such as anhydrous zinc chloride, anhydrous zinc acetate, zinc oxide, acetic acid, hydrochloric acid, and the like.

Numerous different layered photoresponsive imaging members with the perinone pigments illustrated herein can be fabricated. In one embodiment, thus the layered photoresponsive imaging members are comprised of a supporting substrate, an aryl amine hole transport layer, and situated therebetween a vacuum evaporated photogenerator layer comprised of the perinone pigments illustrated hereinbefore. Another embodiment of the present invention is directed to positively charged layered photoresponsive imaging members comprised of a supporting substrate, an aryl amine hole transport layer, and as a top overcoating a vacuum evaporated photogenerator layer comprised of the perinone pigments illustrated hereinbefore. Moreover, there is provided in accordance with the present invention an improved negatively charged photoresponsive imaging member comprised of a supporting substrate, a thin adhesive layer, a photogenerator vacuum evaporated layer comprised of the perinone pigments illustrated herein optionally dispersed in a polymeric resinous binder, and as a top layer aryl amine hole transporting molecules dispersed in a polymeric resinous binder.

The improved photoresponsive imaging members of the present invention can be prepared by a number of methods, the process parameters and the order of coating of the layers being dependent on the member desired. Thus, for example, these imaging members can be prepared by vacuum deposition of the photogenerator layer on a supporting substrate with an adhesive layer thereon, and subsequently depositing by solution coating the hole transport layer. Imaging members suitable for positive charging can be prepared by reversing the order of deposition of the photogenerator and hole transport layes.

Imaging members having incorporated therein the perinone pigments of the present invention are useful in various electrophotographic imaging systems, particularly those conventionally known as xerographic processes. Specifically, the imaging members of the present invention are useful in xerographic imaging processes wherein the perinone pigments absorb light of a wavelength of from about 400 nanometers to about 700 nanometers. In these processes, electrostatic latent images are initially formed on the imaging member followed by development, and thereafter transferring the image to a suitable substrate.

Moreover, the imaging members of the present invention can be selected for electronic printing processes with gallium arsenide light emitting diode (LED) arrays which typically function at wavelengths of 660 nanometers.

BRIEF DESCRIPTION OF THE DRAWINGS

For a better understanding of the present invention and further features thereof, reference is made to the following detailed description of various preferred embodiments wherein.

DESCRIPTION OF THE PREFERRED EMBODIMENTS

Figure 1:
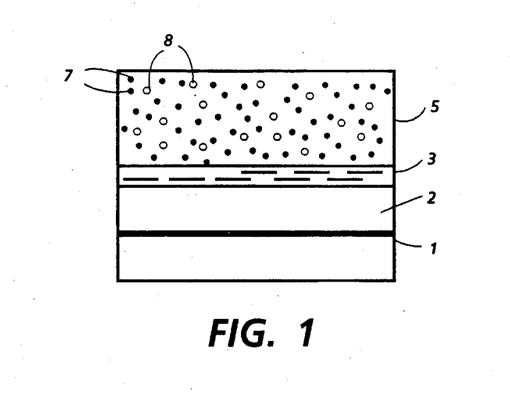
FIG. 1 is a partially schematic cross-sectional view of a negatively charged photoresponsive imaging member of the present invention.

Illustrated in FIG. 1 is a negatively charged photoresponsive imaging member of the present invention comprised of a substrate 1; an adhesive layer 2, a vacuum evaporated photogenerator layer 3 comprised of the cis and/or trans isomer of Formula III, that is trans indanthrene Brilliant Orange (Vat Red 7), cis indanthrene Bordeaux (Vat Red 15), or mixtures thereof with from about 10 to about 90 percent by weight of the cis isomer, available from Hoeschst Chemical Corporation; and a charge transport layer 5 comprised of N,N'-diphenyl-N,N-bis(3-methylphenyl)-[1,1'-biphenyl]-4,4'-diamine components 7 dispersed in a polycarbonate resinous binder 8.

Figure 2:
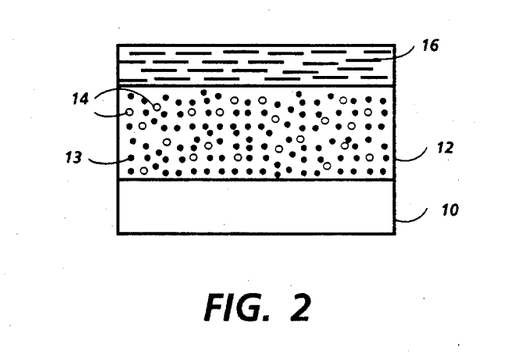
FIG. 2 is a partially schematic cross-sectional view of a positively charged photoresponsive imaging member of the present invention.

Illustrated in FIG. 2 is a positively charged photoresponsive imaging member of the present invention comprised of a substrate 10, a charge transport layer 12 comprised of N,N'-diphenyl-N,N'-bis(3-methylphenyl)-[1,1'-biphenyl]-4,4'-diamine components 13 dispersed in a polycarbonate resinous binder 14, and a photogenerator layer 16 applied by vacuum evaporation comprised of the cis (from about 10 to about 90 percent by weight), and/or trans isomer of the Formula III components.

Similarly, there is included within the scope of the present invention, for example, photoresponsive imaging members as described herein with reference to FIG. 1 with the exception that there can be selected as the photogenerator the perinone pigments of Formulas IV and V, inclusive of bis(4,5-dimethyl)benzimidazole perinone and bis 2,3-naphthimidazole perinone.

Figure 3:
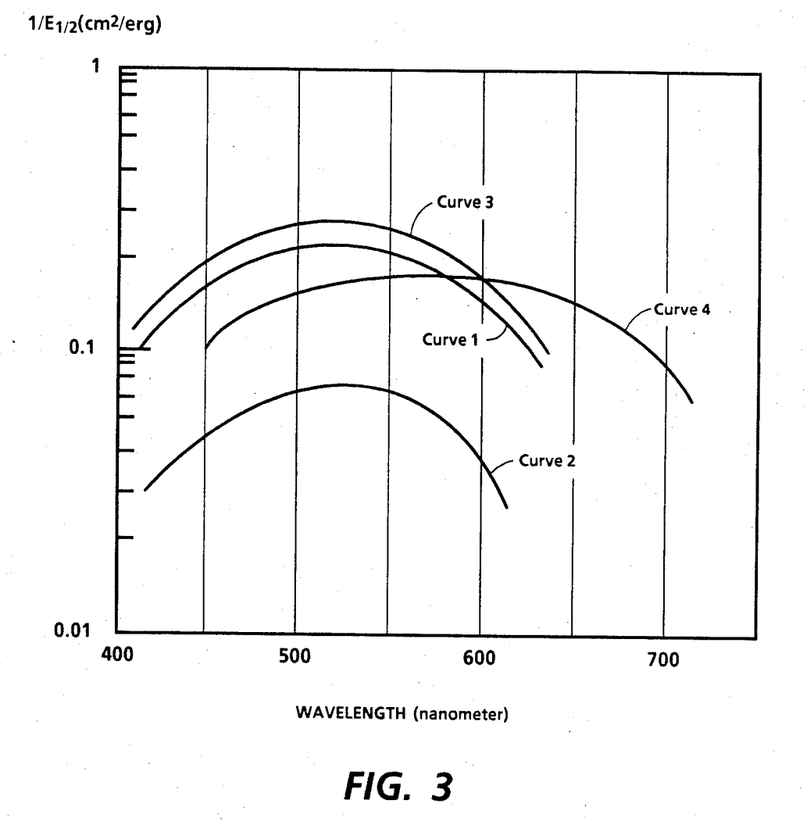
FIG. 3 is a line graph illustrating the spectral response of specific perinone pigments of the present invention.

Illustrated in FIG. 3 is a plot of the $1/E_1$ value versus wavelength in nanometers for photoresponsive imaging members prepared in accordance with Example V. Specifically, curve 1 represents the light sensitivity of the imaging member of the present invention, reference Example V with the cis and trans isomers of Formula III. This sensitivity is substantially (3 times) greater than identical imaging members prepared by the process of the present invention, reference Example V, with the exception that for curve 2 the charge transporting layer consisted of a 15 microns thick layer of poly(N-vinyl carbazole) as described in U.S. Pat. No. 3,879,200. Curve 3 represents the light sensitivity of the imaging member of the present invention, reference Example V, with the cis and trans mixture of bis(4,5-dimethyl)benzimidazole perinone of Formula IV and curve 4 represents the light sensitivity of the imaging member of Example V with the cis and trans mixture of bis(2,3-naphthimidazole)perinone of Formula V. Substantial improvements in photosensitivity and in the red spectral responsive than that for the aforementioned members are indicated as compared to those of U.S. Pat. No. 3,879,200 with a carbazole transport layer.

Substrate layers selected for the imaging members of the present invention can be opaque or substantially transparent, and may comprise any suitable material having the requisite mechanical properties. Thus, the substrate may comprise a layer of insulating material including inorganic or organic polymeric materials, such as Mylar a commercially available polymer; a layer of an organic or inorganic material having a semiconductive surface layer such as indium tin oxide, or aluminum arranged thereon, or a conductive material inclusive of aluminum, chromium, nickel, brass or the like. The substrate may be flexible or rigid and many have a number of many different configurations, such as, for example a plate, a cylindrical drum, a scroll, an endless flexible belt and the like. Preferably, the substrate is in the form of a seamless flexible belt. In some situations, it may be desirable to coat on the back of the substrate, particularly when the substrate is a flexible organic polymeric material, an anti-curl layer such as for example polycarbonate materials commercially available as Makrolon.

The thickness of the substrate layer depends on many factors, including economical considerations, thus this layer may be of substantial thickness, for example, over 2,500 microns; or of minimum thickness providing there are no adverse effects on the system. In one preferred embodiment, the thickness of this layer ranges from about 75 microns to about 250 microns.

With further regard to the imaging members of the present invention, the photogenerator layer is preferably comprised of 100 percent of the perinone pigments disclosed herein. However, providing the objectives of the present invention are achieved, these perinone pigments can be dispersed in resinous binders. Generally, the thickness of the perinone photogenerator layer depends on a number of factors including the thicknesses of the other layers, and the percent mixture of photogenerator material contained in this layer. Accordingly, this layer can be of a thickness of from about 0.05 micron to about 10 microns when the photogenerator perinone composition is present in an amount of from about 5 percent to about 100 percent by volume. Preferably, this layer is of a thickness of from about 0.25 micron to about 1 micron when the photogenerator perinone composition is present in this layer in an amount of 30 percent by volume. In one very specific preferred embodiment, the vacuum deposited photogenerating layers are of a thickness of from about 0.07 micron to about 0.5 micron. The maximum thickness of this layer is dependent primarily upon factors such as photosensitivity, electrical properties and mechanical considerations.

Illustrative examples of polymeric binder resinous materials that can be selected for the photogenerator pigment include those polymers as disclosed in U.S. Pat. No. 3,121,006, the disclosure of which is totally incorporated herein by reference, polyesters, polyvinyl butyral, Formvar ®, polycarbonate resins, polyvinyl carbazole, epoxy resins, phenoxy resins, especially the commercially available poly(hydroxyether) resins, and the like.

As adhesives there can be selected various known substances inclusive of polyesters such as those commercially available from E. I. DuPont as 49,000 polyesters. This layer is of a thickness of from about 0.05 micron to 1 micron. Other layers such as silanes in a thickness of 0.5 to about 1 micron can also be included in the imaging members of the present invention.

Aryl amines selected for the hole transporting layer which generally is of a thickness of from about 5 microns to about 50 microns, and preferably of a thickness of from about 10 microns to about 40 microns, include molecules of the following formula:

dispersed in a highly insulating and transparent organic resinous binder wherein X is an alkyl group or a halogen, especially those substituents selected fromm the group consisting of (ortho) $CH_3$, (para) $CH_3$, (ortho) Cl, (meta) Cl, and (para) Cl.

Examples of specific aryl amines are N,N'-diphenyl-N,N'-bis(alkylphenyl)-[1,1-biphenyl]-4,4'-diamine wherein alkyl is selected from the group consisting of methyl such as 2-methyl, 3-methyl and 4-methyl, ethyl, propyl, butyl, hexyl, and the like. With chloro substitution, the amines is N,N'-diphenyl-N,N'-bis(halophenyl)-[1,1'-biphenyl)-4,4'-diamine wherein halo is 2-chloro, 3-chloro or 4-chloro.

Examples of the highly insulating and transparent resinous material or inactive binder resinous material for the transport layers include materials such as those described in U.S. Pat. No. 3,121,006, the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binders are comprised of polycarbonate resins having a molecular weight of from about 20,000 to about 100,000 with a molecular weight of from about 50,000 to about 100,000 being particularly preferred. Generally, the resinous binder contains from about 10 to about 75 percent by weight of the active material corresponding to the foregoing formula, and preferably from about 35 percent to about 50 percent of this material.

Also, included within the scope of the present invention are methods of imaging with the photoresponsive devices illustrated herein. These methods generally involve the formation of an electrostatic latent image on the imaging member, followed by developing the image with a toner composition, subsequently transferring the image to a suitable substrate, and permanently affixing the image thereto. In those environments wherein the device is to be used in a printing mode, the imaging method involves the same steps with the exception that the exposure step can be accomplished with a laser device or image bar.

The invention will now be described in detail with reference to specific preferred embodiments thereof, it being understood that these examples are intended to be illustrative only. The invention is not intended to be limited to the materials, conditions, or process parameters recited herein, it being noted that all parts and percentages are by weight unless otherwise indicated.

EXAMPLE I

Purified cis benzimidazole perinone of Formula III was isolated by diluting 40 milliliters (ml) of Hoechst Vat Red 15 ink to 600 milliliters (ml) with methanol and centrifuging at 10,000 rpm. The precipitate formed was separated from the supernatant and dried (9.55 grams). The UV-visible absorption spectrum of the resulting pigment in sulfuric acid showed strong absorption maxima at 484, 377, 325, 311, 238, and 208 nanometers. The solid state absorption spectrum of an evaporated film evidenced broad maxima at 520 and 485 nanometers.

EXAMPLE II

Purified trans benzimidazole perinone of Formula III was isolated by filtration of 40 ml Hoeschst Vat Orange 7 ink through a 0.5 micron PTFE ® filter. The precipitate resulting was washed twice with methanol and dried at 110° C. for 4 hours (5.3 grams isolated). The UV-visible absorption spectrum in sulfuric acid for the resulting product evidenced strong maxima at 486, 464 and 384 nanometers. A thin evaporated film showed multiple maxima at 530, 495, 450 and 415 nanometers.

EXAMPLE III

Synthesis of Bis(4,5dimethyl)Benzimidazole Perinone of Formula IV

To a 500 ml liter, 3-necked, round-bottomed flask equipped with a mechanical stirrer, reflux condenser and a nitrogen inlet tube was charged with 1,4,5,8-naphthalene-tetracarboxylic dianhydride (13.41 grams, 0.050 mole), 4,5-dimethyl orthophenylenediamine (34.1 grams, 250 mole) and 1-chloronaphthalene (250 ml). Thereafter, the reaction mixture was heated to 250° C. in about 30 minutes with a heating mantle. Also, the reaction was maintained at 250° C. for 2 hours after which the visible absorption spectrum indicated that the reaction was complete. The resulting product was isolated by filtration, and purification was accomplished by slurrying the product in toluene at 90° C. for 1 hour and filtering. The aforementioned slurry-filter cycle was repeated three times.

Thereafter, the product was dried at 95° C. at −20 inches Hg. vacuum overnight. Yield was 95.6 percent.

The uv-visible absorption of the above product showed a maximum at 534 nanometers ($\epsilon=26,610$), the infrared spectrum evidenced a typical perinone imidazole band at 1697 cm$^{-1}$. The mass spectrum indicated a molecular ion at M/z 468.

| Combustion Analysis: | | | |
|---|---|---|---|
| Calculated (%): | C 76.91 | H 4.30 | N 11.96 |
| Found (%) | C 76.81 | H 4.32 | N 11.99 |

EXAMPLE IV

Synthesis of Bis(2,3naphthimidazole)Perinone Formula V

To a 100 ml flask equipped with a mechanical stirrer and a reflux condenser was charged 1,4,5,8-naphthalene-tetracarboxylic acid dianhydride (4.24 grams, 15.8 millimoles), and 2,3-diaminonaphthalene (5.0 grams, 31.6 millimoles) and acetic acid (25 ml). The reaction was then heated slowly to reflux (1.5 hours) and then heated at reflux for 5 hours. Thin layer chromatography indicated that all of the diaminonaphthalene had reacted to form the corresponding bis imide after the first hour of heating. Cyclization proceeded slowly during the reflux period and ceased after about 50 percent of the bis imide had cyclized (estimated from the infrared spectrum).

The product was isolated by filtration (0.5 micron PTFE ® filter), and was solvent purified by:
1. boiling with acetic acid (300 ml) for 15 minutes, followed by filtration;
2. boiling with acetic acid (50 ml) for 4 hours, followed by filtration.

A portion of the product (3.98 grams) was then train sublimed at 0.1 Torr/487° C.

The yield of naphthimidazole perinone recovered was 42.5 percent (1.69 grams).

The solid state adsorption spectrum for the above in polyvinyl acetate yield absorption maxima at 560 and 630 nanometers respectively. A molecular ion at M/z 512 was observed and the infrared indicated the presence of the perinone imidazole band.

EXAMPLE V

A photoresponsive imaging member was prepared by initially providing an aluminized Mylar substrate in a thickness of 75 microns, followed by applying thereto with a multiple clearance film applicator in a wet thickness of 12.5 microns, and thereover a layer of N-methyl-3-aminopropyl trimethoxysilane, available from PCR Research Chemicals, Florida, in ethanol, in a 1:20 volume ratio. This layer was then allowed to dry for 5 minutes at room temperature, followed by curing for 10 minutes at 110° C. in a forced air oven.

There was then applied to the silane layer 0.5 percent by weight of an adhesive available from DuPont Chemical as 49,000 polyester in methylene chloride and 1,1,2-trichloroethane (4:1 volume ratio) with a multiple clearance film applicator to a wet thickness of 12.5 microns. The layer was allowed to dry for one minute at room temperature and 10 minutes at 100° C. in a forced air oven. The resulting layer had a dry thickness of 0.05 micron. Subsequently, there was deposited thereover with a Varian Model 3117 vacuum coater a photogenerating layer of the cis and trans benzimidazole perinone pigments of Formula III at a final thickness of 0.2 micron. The photogenerator pigment was heated in a tantalum boat to about 350° C., and the vacuum coater evacuated to a pressure of about 10$^{-5}$ Torr. Also, the substrate was mounted 16 centimeters from the boat, and the photogenerator layer was deposited at a rate of about 4 Angstroms/second.

Thereafter, the above photogenerating layer was overcoated with an amine charge transport layer prepared as follows:

A transport layer with 65 percent by weight Merlon, a polycarbonate resin, was mixed with 35 percent by weight N,N'-diphenyl-N,N'-bis(3-methylphenyl)-1,1'-biphenyl-4,4'-diamine, to 7 percent by weight in methylene chloride in an amber bottle. The resulting mixture was then coated in a dry thickness of 15 microns on top of the above photogenerating layer using a multiple clearance film applicator (10 mils wet gap thickness). The resulting member was then dried in a forced air oven at 135° C. for 20 minutes.

The photosensitivity of this member was then determined by electrostatically charging the surface thereof with a corona discharge source until the surface potential, as measured by a capacitively coupled probe attached to an electrometer, attained an initial dark value $V_O$ of $-800$ volts. The front surface of the charged member was then exposed to light from a filtered Xenon lamp, XBO 75 watt source, allowing light in the wavelength range 400 to 800 nanometers to reach the member surface. The exposure causing reduction of the surface potential to half its initial value, $E_\frac{1}{2}$, and the percent discharge of surface potential due to various exposure energies was then determined. The photosensitivity can be determined in terms of the exposure in ergs/cm$^2$ necessary to discharge the member from the initial surface potential to half that value. The higher the photosensitivity, the smaller the exposure energy required to discharge the layer to 50 percent of the surface potential. The photosensitivity spectral response results are illustrated in FIG. 3 where inverse $E_\frac{1}{2}$ is plotted against wavelength in nanometer. With white light, 400 to 700 nanometer exposure, the $E_\frac{1}{2}$ value was found to be 10 ergs/cm$^2$ for the imaging member with the cis isomers and the trans isomers, and the percent discharge at an exposure level of 10 ergs/cm$^2$ was 50. Also, the dark decay was 2 to 7 volts/sec and charge acceptance was 800 volts. For comparison, a photoresponsive element incorporating the same photogenerating pigment, but with a poly(N-vinyl carbazole) hole transport layer instead of the N,N'-diphenyl-N,N'-bis(3-methylphenyl)-1,1'-diphenyl-4,4'-diamine exhibited much lower photosensitivity, that is $E_\frac{1}{2}$ was 31 ergs/cm$^2$ instead of 10 ergs/cm$^2$, and the percent discharge at an exposure level of 10 ergs/cm$^2$ was 18 instead of 50 as follows:

TABLE I

COMPARATIVE RESULTS OF IMAGING DEVICE OF THIS INVENTION WITH THAT OF 3,879,200

| Charge Transport Layer | $E_\frac{1}{2}$ rgs/cm$^2$ | % Discharge at 10 ergs/cm$^2$ | Dark Decay V/sec |
|---|---|---|---|
| Aryl Amine | 10 | 50 | 5 |
| PVK | 31 | 18 | 3 |

EXAMPLE VI

A photoresponsive imaging member was prepared by repeating the procedure of Example V with the exception that there was selected as the photogenerating pigment bis(4,5-dimethyl)benzimidazole perinone in a thickness of 0.2 micron. Thereafter, the photosensitivity of the resulting member was determined by repeating the procedure of Example V with the results of this determination being plotted against various exposure energies. Specifically, with further reference to FIG. 3, at a white light exposure of 400 to 700 nanometers, the $E_{\frac{1}{2}}$ was found to be 8.8 ergs/cm$^2$; and the percent discharge at an exposure level of 10 ergs/cm$^2$ was 60.

EXAMPLE VII

A photoresponsive imaging member was prepared by repeating the procedure of Example V with the exception that there was selected as the photogenerating layer the bis(2,3-naphthimidazole)perinone of Formula V in thicknesses of 0.2 and 0.4 micron, respectively.

The photosensitivity of the resulting member was determined according to the procedure of Example V with the following results:

| Thickness of Photogenerating Layer of Naphthimidazole Perinone | $E_{\frac{1}{2}}$, erg/cm$^2$ | % Discharge at 10 erg/cm$^2$ |
| --- | --- | --- |
| 0.2 micron | 9.2 | 53 |
| 0.4 micron | 6.7 | 64 |

This data indicates that the 0.4 micron member is slightly more sensitive than the 0.2 micron member. Compared with the imaging member of Example V comprised of the mixed benzimidazole perinone photogenerating layer, the 0.2 micron member has slightly higher sensitivity, reference the $E_{\frac{1}{2}}$ values.

The higher sensitivity of imaging members containing the naphthimidazole perinone photogenerator layer is attributed to the wider light absorption range than the range for the benzimidazole perinone.

Most perinones only absorb light in the wavelength region ranging from 400 to 600 nanometers with a maximum absorption occuring at about 480 nanometers. However, the optical absorption spectrum of the Formula V naphthimidazole film vacuum deposited onto a glass slide evidences a broader absorption characteristic of from 400 to 700 nanometers with absorption peaks situated at 520 nanometers. The light absorption property beyond 600 nanometers enables the naphthimidazole perinone to capture more light, especially from the white light generated in xerographic processes. Also, imaging member with the naphthimidazole perinone can be used in conjunction with a 630 nanometers He/Ne laser commonly selected for electronic printing processes. Similarly, the benzimidazole perylene imaging element can be selected for use with GaAsP light emitting diode (LED) arrays operating at a wavelength of 660 nanometers in electronic printers.

Other modifications of the present invention may occur to those skilled in the art based upon a reading of the present disclosure and these modifications, including equivalents thereof, are intended to be included within the scope of the present invention.

What is claimed is:

1. An improved layered photoresponsive imaging member comprised of a supporting substrate; a photogenerator layer comprised of a perinone as represented by the following formula wherein R is selected from the group consisting of hydrogen substituent, alkyl, aryl, substituted alkyl, and substituted aryl; and an aryl amine hole transport layer comprised of molecules of the following formula:

dispersed in a resinous binder and wherein X is selected from the group consisting of halogen and alkyl.

2. An imaging member in accordance with claim 1 wherein the supporting substrate is comprised of a conductive metallic substance, or an insulating polymeric composition overcoated with an electrically conductive layer.

3. An imaging member in accordance with claim 1 wherein the supporting substrate is aluminum.

4. An imaging member in accordance with claim 1 wherein the supporting substrate is overcoated with a polymeric adhesive layer.

5. An imaging member in accordance with claim 4 wherein the adhesive layer is a polyester resin.

6. An imaging member in accordance with claim 1 wherein X is selected from (ortho) CH$_3$, (meta) CH$_3$, (para) CH$_3$, (ortho) Cl, (meta) Cl, and (para) Cl.

7. An imaging member in accordance with claim 1 wherein the aryl amine is N,N'-diphenyl-N,N'-bis(3-methylphenyl)-[1,1'-biphenyl]-4,4'-diamine.

8. An imaging member in accordance with claim 1 wherein the resinous binder is a polycarbonate or polyvinylcarbazole.

9. An imaging member in accordance with claim 1 wherein the perinones are dispersed in a resinous binder in an amount of from about 5 percent to about 95 percent by volume, and the aryl amine hole transport molecules are dispersed in a resinous binder in an amount of from about 10 to about 75 percent by weight.

10. An imaging member in accordance with claim 9 wherein the resinous binder for the perinones is a polyester, polyvinylcarbazole, polyvinylbutyral, a polycarbonate, or a phenoxy resin; and the resinous binder for the aryl amine hole transport material is a polycarbonate, a polyester, or a vinyl polymer.

11. A imaging member in accordance with claim 1 wherein the aryl amine hole transport layer is situated between the supporting substrate and the photogenerating layer.

12. An improved layered photoresponsive imaging member which comprises a supporting substrate, a photogenerator layer comprising a perinone as represented by the following formula and an aryl amine hole transport layer comprising molecules of the following formula:

dispersed in a resinous binder and wherein X is selected from the group consisting of halogen and alkyl.

13. An imaging member in accordance with claim 12 wherein the perinones are of the following formula 14. An imaging member in accordance with claim 12 wherein the perinones are of the following formula 15. An imaging member in accordance with claim 13 wherein the supporting conductive substrate is overcoated with a thin polymeric adhesive layer.

16. An imaging member in accordance with claim 15 wherein the aryl amine charge transporting layer comprises molecules of the formula:

dispersed in a resinous binder, and wherein X is selected from the group consisting of halogen and alkyl.

17. An imaging member in accordance with claim 16 wherein X is selected from (ortho) $CH_3$, (meta) $CH_3$, (para) $CH_3$, (ortho) Cl, (meta) Cl, and (para) Cl.

18. An imaging member in accordance with claim 16 wherein the aryl amine is N,N'-diphenyl-N,N'-bis(3-methylphenyl)-[1,1'-biphenyl]-4,4'-diamine.

19. An imaging member in accordance withh claim 16 wherein the resinous binder is a polycarbonate or polyvinyl carbazole.

20. An imaging member in accordance with claim 16 wherein the perinones are dispersed in a resinous binder in an amount of from about 5 percent to about 95 percent by volume, and the aryl amine hole transport molecules are dispersed in a resinous binder in an amount of from about 10 to about 75 percent by weight.

21. A method of imaging which comprises forming an electrostatic latent image on the imaging member of claim 1, causing development thereof with toner particles; subsequently transferring the developed image to a suitable substrate; and permanently affixing the image thereto.

22. A method of imaging which comprises forming an electrostatic latent image on the imaging member of claim 12, causing development thereof with toner particles, subsequently transferring the developed image to a suitable substrate; and permanently affixing the image thereto.

23. A method of imaging which comprises forming an electrostatic latent image on the imaging member of claim 13, causing development thereof with toner particles; subsequently transferring the developed image to a suitable substrate; and permanently affixing the image thereto.

24. A method of imaging which comprises forming an electrostatic latent image on the imaging member of claim 14, causing development thereof with toner particles; subsequently transferring the developed image to a suitable substrate; and permanently affixing the image thereto.

25. An imaging member in accordance with claim 1 wherein the perinone is comprised of a mixture of the cis and trans isomers of bis(4,5-dimethyl)benzimidazole perinone.

26. An imaging member in accordance with claim 12 wherein the perinone is trans indanthrene Brilliant Orange.

27. An imaging member in accordance with claim 12 wherein the perinone is cis indanthrene Bordeaux RR.

28. An imaging member in accordance with claim 12 wherein the perinone is comprised of a mixture of trans indanthrene Brilliant Orange and indanthrene Bordeaux RR.

29. An imaging member in accordance with claim 12 wherein the perinones are of the following formula 30. An imaging member in accordance with claim 12 wherein the perinone is comprised of a mixture of cis and trans isomers of Formula I.

* * * * *